United States Patent
Marx et al.

(10) Patent No.: US 7,531,351 B2
(45) Date of Patent: May 12, 2009

(54) LIQUID-GAS-PHASE EXPOSURE REACTOR FOR CELL CULTURING

(75) Inventors: Uwe Marx, Berlin (DE); Marco Riedel, Berlin (DE); Hikmat Bushnaq-Josting, Berlin (DE)

(73) Assignee: ProBioGen AG, Berlin (DE)

( * ) Notice: Subject to any disclaimer, the term of this patent is extended or adjusted under 35 U.S.C. 154(b) by 327 days.

(21) Appl. No.: 11/151,345

(22) Filed: Jun. 14, 2005

(65) Prior Publication Data

US 2006/0019391 A1 Jan. 26, 2006

Related U.S. Application Data

(60) Provisional application No. 60/578,824, filed on Jun. 14, 2004.

(51) Int. Cl.
*C12M 1/12* (2006.01)
*C12M 3/00* (2006.01)
*C12M 1/00* (2006.01)
*C12P 21/06* (2006.01)

(52) U.S. Cl. ............. 435/297.4; 435/69.1; 435/285.1; 435/289.1; 435/297.1

(58) Field of Classification Search ............ 435/297.4, 435/69.1, 285.1, 291.8, 289.1, 297.2, 297.3, 435/297.1
See application file for complete search history.

(56) References Cited

U.S. PATENT DOCUMENTS

| | | | |
|---|---|---|---|
| 3,997,396 A | | 12/1976 | Delente |
| 4,804,628 A | | 2/1989 | Cracauer et al. |
| 5,064,764 A | * | 11/1991 | Besnainon et al. ........ 435/297.4 |
| 5,282,964 A | * | 2/1994 | Young et al. .............. 210/321.8 |
| 5,516,691 A | | 5/1996 | Gerlach |
| 5,712,154 A | * | 1/1998 | Mullon et al. ............. 435/297.4 |
| 5,955,353 A | * | 9/1999 | Amiot ...................... 435/297.4 |
| 2002/0197713 A1 | * | 12/2002 | Cadwell ...................... 435/325 |
| 2004/0096943 A1 | * | 5/2004 | Marx et al. ................. 435/69.1 |

FOREIGN PATENT DOCUMENTS

| | | |
|---|---|---|
| DE | 2431450 | 1/1975 |
| DE | 4230194 A1 | 3/1994 |
| WO | WO/03/064586 A2 | 8/2003 |
| WO | WO 03/102123 A2 | 12/2003 |

OTHER PUBLICATIONS esp@cenet~ English Abstract of DE4230194, Mar. 10, 1994.
esp@cenet—English Abstract of DE2431450, Jan. 23, 1975.
esp@cenet—English Abstract of WO03064586, Aug. 7, 2003.
esp@cenet~ English Abstract of WO03102123, Dec. 11, 2003.

* cited by examiner

*Primary Examiner*—Walter D Griffin
*Assistant Examiner*—Lydia Edwards
(74) *Attorney, Agent, or Firm*—Oblon, Spivak, McClelland, Maier & Neustadt, P.C.

(57) ABSTRACT

Initiation of growth and cultivation of cells can be performed by introducing the cells into culture compartments of a liquid-gas-phase exposure bioreactor containing a supply chamber in which there are disposed hollow-filament membranes having an inside diameter of no larger than 5 mm, wherein an inner volume of said hollow-filament membranes forms the culture compartments. Approximately one half of the supply chamber is filled with a nutrient medium and a remainder is filled with a gas mixture. Perfusion of medium and gas is turned on simultaneously or separately. The hollow-filament membranes and the cells contained therein are cyclically exposed to the gas or liquid phase.

10 Claims, 1 Drawing Sheet

LIQUID-GAS-PHASE EXPOSURE REACTOR FOR CELL CULTURING

BACKGROUND OF THE INVENTION

1. Field of the Invention

The present invention relates to a method and a device for initiation of cell growth and for cultivation of cells in high densities. The cells to be cultivated are located in hollow-filament membranes and are brought alternately into a liquid nutrient medium and a gas phase.

2. Description of the Related Art

Mammalian cell cultivation for the synthesis of biopharmaceutical drugs is performed mainly in stirred reactors. Heretofore, airlift reactors have been used less frequently and hollow-fiber reactors very rarely for servicing the market with drugs based on mammalian cells. To improve the volumetric product yields in stirred reactors, the cell density and the effective production time of the cells are increased by optimizing the methods and using nutritional regimens specific to the cell lines in fed batch methods. The production technology is laid out in bioreactor trains containing three to four stirred reactors, each with a volumetric capacity of approximately five times that of the preceding bioreactor. The largest available stirred reactor for cultivation of mammalian cells currently has a volumetric capacity of 20,000 liters. Fed-batch processes in stirred reactors are robust, can be scaled up to the above volumes and long ago were accepted by the authorities for drug synthesis. Disadvantages are the long dwell times of the products in the culture chamber, the need for separation of cells from the harvest supernatant, the cleaning and sterilization expenses incurred during multiple use and the high investment and operating expenses for plants equipped with this technology.

For proteins, such as human factor VII, a protein of the clotting cascade, which are susceptible to degradation and thus impose a short dwell time in the bioreactor during synthesis, there have been developed devices and systems that permit perfusion of the culture chamber and thus continuous operation of the stirred reactors. For this purpose, efficient cell retention with continuous media feed and product harvesting is necessary. Spin filters are used here in the interior chamber of the stirred reactor, while support materials in the form of fluidized or stationary beds are used in the traps, where the production cells can adhere to surfaces. The continuous mode of operation of stirred reactors can also be achieved via external cell-retention systems, such as cell sedimentation, continuous cell centrifugation or ultrasonic cell collection. Advantages of the continuous mode of operation are short product dwell times in the bioreactor, constant product quality during synthesis, increase of the volumetric productivity and greater flexibility of batch volume as a function of the cultivation time to be defined. Disadvantages are contamination of the harvest with residual cells, the cleaning and sterilization expenses incurred for multiple use and the high investment and operating costs for the corresponding plants.

Besides the hollow-fiber bioreactors of ACUSYST® X Cell Generation, which have proved effective for the synthesis of biopharmaceuticals, other reactor systems are available in which all components coming in contact with the cell culture are designed as disposable components. Thus they can be discarded once they have been used to synthesize a batch. Expensive cleaning and sterilization procedures are not required. Commercially available systems of this type are membrane-based systems such as Cell-Pharm®, Cellmax®, Technomouse®, CELLine®, miniPERM® or OptiCell®. Membrane methods have several advantages. In perfusion operation they can achieve very high cell densities ($10^7$ to $10^8$ cells/ml)—by virtue of a large membrane surface per unit volume. Moreover, the cells are protected by the membranes from shearing forces. In principle, they are designed for one-time use, so that cleaning and sterilization after use are not necessary. In the art of disposable bioreactors, the wave bioreactor has also proved effective heretofore in the trial phase for the synthesis of biopharmaceuticals. In the system, the cells are cultivated in a bag system, which is systematically agitated in order to improve intimate mixing. One advantage of this reactor technology is the one-time usability of the culture system. Disadvantages are the low achievable densities and the limited scale-up capability.

In all cited methods and devices, uniform nutrient supply and in particular oxygen supply at high cell densities is problematic. Neither the attempt to solve this problem via complex process steps involving pressurization (1989, U.S. Pat. No. 4,804,628 A) nor the direct introduction of oxygen into the cell culture chamber via a further membrane system (1986, DE 2431450 A1 and 1995, DE 4230194 A1) led to culture systems whose scale could be increased as desired and in which the cells could be uniformly supplied. In hollow-fiber bioreactors, in which the cells are cultivated between the hollow fibers and the nutrients are transported in the lumen of the fibers, scale-up is limited by the length of the hollow fibers. However, the length of the hollow fibers is limited by consumption of the oxygen from the hollow fibers. Thereby scale-up is possible only by the use of parallel units. In practice, however, this leads to unprofitable processes. In other words, the scale-up capability of the hollow-fiber reactors is defeated by the lack of adequate homogeneous supply of the cells with fresh gas and liquid nutrient components.

In WO 03/064586 A2, it was proposed that cells be cultivated in high density in compartments, the dimension of which compartments is not to exceed 5 mm in length. The interior chamber of the compartments forms a culture chamber, which is partitioned from the supply chamber by a semipermeable element. The cells are retained in the compartments, and oxygen exchange takes place via hollow-fiber membranes. Supply of the cells with nutrients and with oxygen is ensured by means of a variably adjustable mixture of gas and cell-culture media. Although the culture device and the method solve the problem of nutrient and oxygen supply and guarantee scale-up capability, the method described in WO 03/064586 A2 suffers from a disadvantage in that cells of high density must be introduced into the compartments. To overcome this disadvantage, it was proposed in WO 03/102123 A2 that biodegradable gels be used to reduce the inoculation density at the beginning of cell cultivation.

A liquid-gas-phase exposure bioreactor has been developed in principle by the Zellwerk® Co. and is being sold by the Sartorius® Co. In this bioreactor, the cells that adhere to surfaces are immobilized on disks of carrier material. The disks are disposed in series on a shaft, and are rotated in a cylinder that is half-filled with medium and half-filled with gas. An advantage of this arrangement is the cyclic exposure of these cells to both phases. Disadvantages are the limitation of the system and method to adhering cells, the presence of detached cells in the harvest fluid and the limitation of scale-up capability.

SUMMARY OF THE INVENTION

It is an object of the present invention is to provide a method for initiation of cell growth and for cultivation of cells in high densities.

It is another object of the present invention to provide a device for initiation of cell growth and for cultivation of cells in high densities.

It is yet another object of the present invention to provide a method in which the cells are exposed to two different phases. This and other objects have been achieved by the present invention the first embodiment of which includes a method for initiation of growth and cultivation of cells, comprising:

introducing said cells into culture compartments of a liquid-gas-phase exposure bioreactor comprising
a supply chamber comprising hollow-filament membranes having an inside diameter of no larger than 5 mm, wherein an inner volume of said hollow-filament membranes forms said culture compartments;
filling approximately one half of said supply chamber with a nutrient medium and a remainder with a gas mixture, thereby obtaining a gas phase and a liquid phase;
turning on perfusion of medium and gas simultaneously or separately;
cyclically exposing said hollow-filament membranes and said cells contained therein to the gas or liquid phase.

In another embodiment, the present invention provides a device, comprising:

a cylindrical two-phase supply chamber which can be charged with gas and a culture medium,
parallel to the longitudinal axis of a shell of said supply chamber, polymeric, cell-retaining, microfiltering, hollow-filament membranes having an inside diameter of not more than 5 mm are fixed in an end plate, wherein the inner volumes of said hollow-filament membranes form culture compartments in which cells to be cultivated are disposed,
wherein the supply chamber contains a gas phase through which a gas mixture can flow and a liquid phase through which said culture medium can flow;
wherein each hollow-filament membrane has a spacing of at least 0.5 mm to the neighboring hollow-filament membrane over the length of the cylinder;
wherein the hollow-filament membranes are symmetrically disposed relative to an imaginary cross section along the longitudinal axis of the cylinder;
wherein no membrane is disposed on the imaginary cross-sectional plane along the longitudinal axis of the cylinder;
wherein said device is capable of being used for initiation of growth and cultivation of cells.

DETAILED DESCRIPTION OF THE PREFERRED EMBODIMENTS

Figure 1:
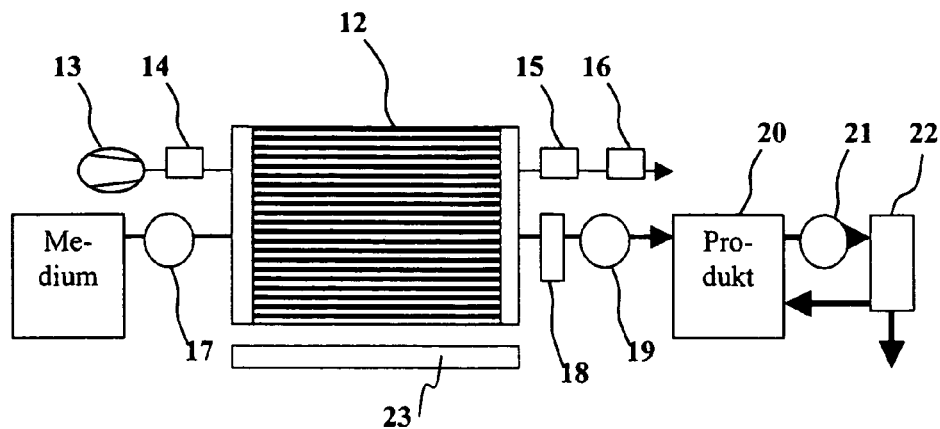
FIG. 1 is a schematic diagram of the bioreactor system.

In the context of the present invention, the following phrases are understood to mean the following. A culture with high cell density ("cells of high density") is achieved at cell densities greater than $1e^7$ cells per milliliter of culture chamber. "Cells of low density" are achieved when the cell density in the culture chamber lies between $1e^4$ and $1e^7$ per milliliter of culture chamber. A culture with the lowest cell density ("cells of lowest density") is achieved at densities lower than $1e^4$ cells per milliliter of culture chamber. A "nutrient medium" is an aqueous solution containing the nutrients essential for the cells, such as glucose, amino acids and trace elements. In the present invention, a gas mixture preferably describes a mixture comprising air and carbon dioxide with variable mixing ratio. Furthermore, the present meaning of the term gas mixture also includes variable mixing ratios of nitrogen, oxygen and $CO_2$.

According to the present invention, the initial growth and cultivation of cells is undertaken in a liquid-gas-phase exposure bioreactor containing a supply chamber in which there are disposed hollow-filament membranes having an inside diameter of no larger than 5 mm and whose inner volume forms culture compartments. The following process steps take place:

introduction of the cells into the culture compartments;
preferably filling approximately or about one half of the supply chamber with a nutrient medium and the other half with a gas mixture;
turning on perfusion of medium and gas simultaneously or separately; and
cyclic exposure of the hollow-filament membranes and of the cells contained therein in the gas or liquid phase.

In a preferred embodiment of the method according to the present invention, the hollow-filament membranes are oriented horizontally in the bioreactor. After the reactor has been filled, half of the membranes are covered with nutrient medium. By rotating the reactor 360° in one direction and then in the opposite direction, cyclic exposure of the hollow-filament membranes and thus of the cells in the gas or liquid phase is achieved.

The filling of the supply chamber may be to a level of from about 45% to about 55%. The filling level of the supply chamber includes all values and subvalues therebetween, especially including 245, 46, 47, 48, 49, 50, 51, 52, 53, 54 and 55% of the total volume of the supply chamber.

Rotation in one direction and then in the opposite direction prevents the tubing connected to the reactor from becoming twisted.

According to the present invention, the rotation is stopped for a certain time after 180° C., in order to achieve equal exposure times in the gas and liquid phases. The holding times can be variably adjusted. Thereby it is ensured that the cells are supplied sufficiently with nutrients during the dwell time of the membranes in liquid nutrient medium and sufficiently with oxygen during the dwell time in the gas phase. By varying the holding times, it is simultaneously possible to adapt to the individual metabolic requirements of the individual cell lines.

The holding times are preferably between 1 second and 1 hour. The holding time includes all values and subvalues therebetween, especially including 2, 3, 4, 5, 10, 15, 20, 25, 30, 35, 40, 45, 50, 55 seconds, and 1, 5, 10, 15, 20, 25, 30, 35, 40, 45, 50, and 55 minutes.

Alternatively, the cyclic exposure of the hollow-filament membranes can be achieved by immersing the hollow-filament membranes in the nutrient medium and then lifting them into the gas phase. Different dwell times of the cells in the two phases can be achieved by this procedure.

To implement the method according to the present invention, cells of low density are first introduced into the culture chamber, whereupon they grow to cells of high density. By using gels—as described in WO 03/102123 A2—it is possible to introduce, into the culture chamber, cells of the lowest cell density together with gels of cross-linked polypeptides, which have a high glutamine content, and/or with semisolid media of viscous fluids or fluids comprising microscopically small gel fragments.

The cells are introduced into the compartments via a central charging system outside the supply chamber, so that simultaneous uniform input of the cells into all compartments is possible via one port.

The method according to the present invention is suitable for cultivating protozoa, bacteria, yeasts, fungi and plant or mammalian cells.

In contrast to the method of the present invention, WO 03/064586 A2 fails to disclose or suggest exposure of the cells in two different phases. WO 03/064586 A2 merely exposes the cells in a variably adjustable mixture of gas and cell culture media. Also, no movement of the reactor or of the membranes was described in WO 03/064586 A2. Not even a hint that the membranes containing the cells can be moved for certain times in the corresponding phases is obtained from WO 03/064586 A2. One reason is that in WO 03/064586 A2 needs a device for production of the variably adjustable mixture of gas and cell culture media, and so movement of the membranes—especially by rotation—would necessitate further complicated provisions with respect to the connections.

The device according to the present invention comprises a cylindrical or spherical two-phase supply chamber. The chamber can be charged with gas and medium respectively. Parallel to the longitudinal axis of the cylinder shell or as appropriate in the spherical shell, polymeric, cell-retaining, microfiltering, hollow-filament membranes having an inside diameter of no more than 5 mm are fixed in the end plates, the inner volumes of which form culture compartments, in which the cells to be cultivated are disposed. The supply chamber contains a gas phase through which a gas mixture can flow and a liquid phase through which a culture medium can flow. Each hollow-filament membrane has a spacing of at least 0.5 mm to the neighboring hollow-filament membrane over the length of the cylinder. The hollow-filament membranes are symmetrically disposed relative to an imaginary cross section along the axis of rotation of the cylinder. No membrane is disposed on an imaginary cross-sectional plane along the axis of rotation of the cylinder.

The membranes are permeable for all substances but not for whole cells. The culture chamber, comprising the total volume of the compartments, is partitioned from the supply chamber by the membrane. This permits the supply substrates to pass into the culture chamber and supply the cells. The partition system also permits products to pass out of the cell compartments into the supply environment.

The membrane comprises polymers, such as polysulfone, polyether sulfone or polycarbonate. Hollow-filament membranes that comprise polyether sulfone, which is a biocompatible material, and that have membrane wall thicknesses smaller than 300 µm, water permeabilities of greater than 6 $m^3/m^2 \cdot h \cdot bar$, preferably greater than 8 $m^3/m^2 \cdot h \cdot bar$, more preferably greater than 10 $m^3/m^2 \cdot h \cdot bar$, and pore diameters of 0.1 to 5.0 µm have proved to be particularly suitable. The wall thickness includes all values and subvalues therebetween, especially including 1, 5, 10, 15, 20, 25, 50, 75, 100, 125, 150, 175, 200, 225, 250, 275 and 295 µm. The pore diameter includes all values and subvalues therebetween, especially including 0.5, 1, 1.5, 2, 2.5, 3, 3.5, 4, and 4.5 µm.

To prevent the formation of liquid films and thus to ensure uniform exposure of the membranes in the gas phase, the membranes have a minimum spacing relative to one another.

The membranes are preferably disposed in a hexagonal array. This means that every membrane—with the exception of those located at the outer peripheries—is surrounded by 6 membranes with the same spacing relative to the central membrane. Thus the most uniform possible packing density can be ensured in the supply chamber. Further space-saving devices are not necessary.

The hollow-filament membranes are symmetrically arranged relative to an imaginary cross section along the axis of rotation of the cylinder—which for practical purposes represents the phase boundary. No membranes are located on the imaginary cross-sectional plane along the axis of rotation of the cylinder. In this way it is ensured that, during the holding times, all membranes are either completely in the gas phase or completely in the liquid phase.

In contrast to the present invention, WO 03/064586 A2 fails to disclose or suggest a device with two-phase operation. Furthermore, the device of the present invention does not need any special device for production of a mixture of gas and media or for collection of liquid from the spent mixture of gas and media.

For input and removal of gas, every end plate of the cylinder contains at least two ports, which are respectively disposed above and below the imaginary cross-sectional plane, so that continuous supply with gas is ensured even during rotation of the cylinder around its axis of rotation.

Furthermore, at least one tubing port for media perfusion and at least one inlet for introduction of seed cells into the culture chamber are disposed on the head faces.

In addition, the device may optionally contain at least one of the following: tubings, gas humidifiers, a medium trap in the gas line, an ultrafiltration unit in a product-harvesting line, a hardware unit, pumps, measuring and control units as well as a drive motor and a frame, to permit mounting and rotation of the device.

The purpose of the ultrafiltration unit in a product-harvesting line is to concentrate the respective product.

Surprisingly, it has been found that a higher cell density and thus a higher yield of cell products can be achieved with the device according to the present invention than with the device according to WO 03/064586 A2. This can be attributed on the one hand to the optimal use of space and on the other hand to the improved supply of the cells by cyclic exposure of the hollow-filament membranes in the two phases.

Alternatively, the ports for the gas supply are mounted not on the head faces but on the cylinder shell, above and below the imaginary cross-sectional plane.

The device of the present invention can be used in the cultivation of cells at high densities and in the recovery of cell products—such as membrane vesicles; viruses—such as herpes-virus or pox-viruses; proteins—such as antibodies, fusion proteins or profactors; low molecular weight products—such as lactate or aminoacids or drugs as well as diagnostic and research reagents; cell constituents—such as phospholipids or glycolipids. The low molecular weight substances are preferably substances (compounds) with a molecular weight lower than 8 kDa (kiloDalton). The cell products, cell constituents, viruses, proteins or low molecular weight substances are prepared by the cells in the membranes. The cell products etc. are introduced through the membranes into the liquid medium in the supply chamber of the reactor and then removed with the liquid medium from the reactor. Outside the reactor, the cell products, cell constituents, viruses, proteins or low molecular weight substances, are separated from the liquid by, for example, filtration, microfiltration, or distillation. Other separation techniques are possible.

The present invention achieves effective continuous cultivation of cells in high densities and recovery of products from these cells with simultaneous cell retention.

The present invention and its function will be explained hereinafter with reference to figures which are provided herein for purposes of illustration only, and are not intended to be limiting unless otherwise specified.

In the figures, the following reference numerals are used.

| | |
|---|---|
| 1 | Feed end plate |
| 2 | Discharge end plate |
| 3, 4 | Ports for gas supply and removal |
| 5 | Gas phase |
| 6 | Liquid phase |
| 7 | Phase boundary |
| 8 | Inlet for medium (central port) |
| 9 | Central port for product discharge |
| 10 | Ports for the culture chamber |
| 11 | Cell-distributing chambers |
| 12 | Cylindrical supply chamber |
| 13 | Gas-mixing station |
| 14 | Gas humidifier |
| 15 | Media trap |
| 16 | Contamination trap |
| 17, 19, 21 | Pumps |
| 22 | Ultrafiltration module |
| 23 | Rotary device |

FIG. 1 is a schematic diagram of the bioreactor system. FIG. 1 represents one embodiment of the bioreactor system on the basis of a cylindrical supply chamber (12). The alignment but not the real dimensions and actual number of hollow-filament culture compartments disposed in the supply chamber is represented by the black lines in the supply chamber. The cylindrical vessel is driven by a rotary device (23) such that its direction of movement alternates periodically at a suitable rhythm. The flow of gas phase through the supply chamber is ensured by a gas line, which comprises a gas-mixing station (13) and a gas humidifier (14) for the gas feed into the cylinder and of a media trap (15) and a contamination trap (16) for the gas discharge out of the cylinder. The flow of liquid phase through the cylinder is ensured by a media line, which comprises the media reservoir and a pump (17) for the media feed and a pump (19) and the product-collecting vessel (20) for the discharge from the cylinder. Furthermore, a measuring-sensor train (18) for measuring the oxygen, pH and temperature is integrated in the discharge line. A circulation containing a pump (21) and an ultrafiltration module (22) is connected to the product-collecting vessel for concentration of the product in the product-collecting vessel (20). The product-free filtrate is discharged at the bottom of this ultrafiltration module and discarded, while the concentrated product is recycled to the product-collecting vessel. Advantageously, all elements of the bioreactor system, beginning with the port on the gas-mixing station, are disposable materials. The pumps are designed as hose pumps.

Figure 2:
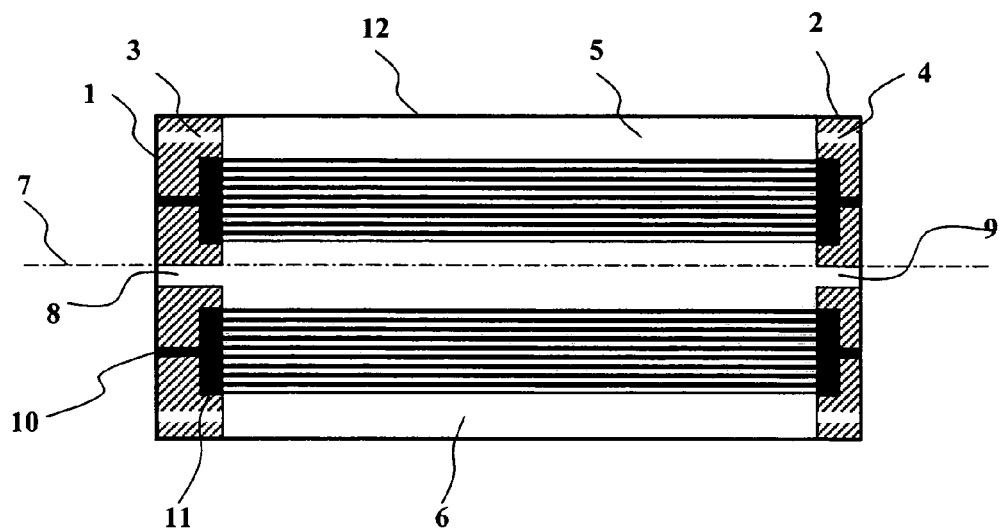
FIG. 2 shows a longitudinal section of the cylindrical two-phase supply chamber.

FIG. 2 shows a longitudinal section of the cylindrical two-phase supply chamber. During reactor operation, the cylindrical supply chamber (12) contains a gas phase (5) in the upper part and a liquid phase (6) in the lower part, the two phases forming a phase boundary (7). On the left, the supply chamber is terminated by an end plate (1) for the feed of gas and medium, and on the right it is terminated by an end plate (2) for discharge thereof. Gas is passed through ports (3, 4) in the end plates. Media transport takes place via central ports (8, 9), located on the axis of rotation of the cylinder, in the respective end plates. The individual culture compartments for the cells are designed as identical hollow-filament membranes and are represented in the supply chamber by parallel black lines. Input of the cell suspension takes place separately from the gas and media supply, via ports (10) shown in solid black in the end plates. For uniform seeding with the cells in all hollow-filament membranes, the ports end in cell-distributing chambers (11), which are in communication with the interior space of every individual hollow-filament membrane.

Figure 3:
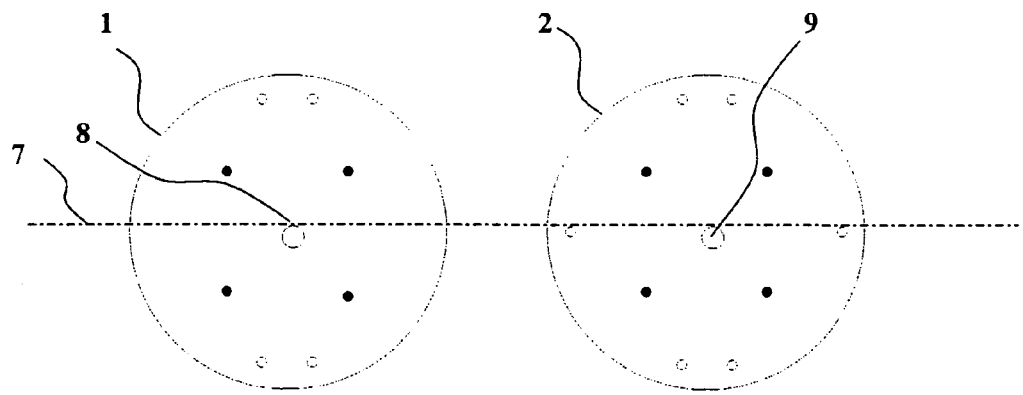
FIG. 3 shows a top view of the end plates of the supply chamber.

FIG. 3 shows a top view of the end plates of the supply chamber. In the top view of the feed end plate (1) there is illustrated one of the arrangements used for the inlets for gas, shown as small circles, and for medium (8) into the supply chamber. The top view of discharge end plate (2) shows the central port for product discharge (9) and an arrangement used for the gas-discharge ports, which are shown as small circles. In this example four ports, represented by black dots, for seeding with the cell suspension are integrated in each of the two end plates, which can be charged via a merged tubing connection.

Having generally described this invention, a further understanding can be obtained by reference to certain specific examples which are provided herein for purposes of illustration only, and are not intended to be limiting unless otherwise specified.

EXAMPLES

Example 1

Cells of High Density

Two bioreactor systems were constructed according to the scheme illustrated in FIG. 1. The cylindrical supply chamber had a total volumetric capacity of 14 liters. During the process, the liquid phase contained 7 liters. In both cases, 144 hollow-filament membranes each 500 mm in length were disposed in axially symmetric arrangement in the supply chamber. Seeding with cells in the interior spaces of the hollow-filament membranes took place with cells of high density in PBG 1.0 basic medium (a synthetic mammalian cell culture medium comprising a wide number of compounds) containing 0.02% of added human serum albumin via the seeding ports in the end plates. The cell line produces a human protein, which can be isolated from the culture supernatant by a one-step chromatographic method and then assayed exactly as to its content. The culture time was 10 and 23 days. Over this time, a mixture of air and 5% $CO_2$ was passed continuously through the gas phase of the supply chamber. In total, a quantity corresponding to 11 liters in 10 days and 24 liters in 23 days was used to supply the cells in the runs. During the experiment, the liquid-phase and gas-phase exposure cycles were each 30 seconds between the phase alternations. After completion of culturing, the cells were harvested from the hollow-filament membranes via the seeding ports and the cell density and viability were determined. The protein was isolated from an aliquot of the cell-free product harvest and its content was assayed. The following table shows the cell density and viability achieved in the hollow-filament culture compartments.

| | Bioreactor run 1 (10 days) | Bioreactor run 2 (23 days) |
|---|---|---|
| Total cell count in inoculum [cells per ml of culture chamber] | 1.5E7 | 1.8E7 |
| Viability of inoculum [%] | 67 | 80 |
| Total cell count of harvest | 2.4E7 | 2.25E7 |
| Viability of harvest (%) | 54 | 29 |
| Total quantity of protein (mg) | 48 | 168 |

High cell densities were successfully achieved in the system. Furthermore, 48 mg and 168 mg of protein were formed during the process and were collected from the cell-free culture supernatant into the corresponding product-collecting vessel.

Example 2

Cells of Low Density

Cells in living cell densities of $1.3e^5$ cells per milliliter of culture chamber were used for inoculation in two two-phase exposure reactors, each containing 12 hollow-filament membranes having a length of 200 mm, and were cultivated for 4 days while both plastic reactors were being rotated. Prior to inoculation, the cells were mixed with microscopically small gel fragments of HAS (human serum albumin). Media exchange was effected discontinuously. The metabolic activity was measured via the glucose consumption. After completion of the runs, the cell densities were determined by harvesting the gel together with the cells contained therein and counting via Trypan Blue. Within the short culture time, expansion of the cells to $6e^5$ living cells per milliliter of culture chamber (4.6 times) and $5e^5$ living cells per milliliter of culture chamber (3.8 times) was successfully achieved.

Example 3

Functioning Principle of the Bioreactor System

The supply principle of the bioreactor is based on exposing the cells alternately in medium and in a gas mixture, thus making it possible to improve the supply of the cells with oxygen compared with conventional systems.

Example 4

Construction of the System

The core piece of the bioreactor was a cylindrical plastic reactor mounted horizontally. In this vessel, hollow-filament membranes were clamped over the length, parallel to the axis of rotation, as illustrated in FIG. 2. Hereby, two chambers separated from one another by the membranes were created in the cylinder. One was the supply chamber, which surrounds the hollow-filament membranes and comprises a liquid phase and a gas phase. The boundary between these two phases is sketched in FIGS. 2 and 3. The other was the space inside each hollow-filament membrane. The sum of all hollow-filament internal spaces represented the culture chamber for the cells. Via the number of hollow-filament membranes disposed symmetrically around the axis of rotation, the system could be scaled-up to any desired size in terms of its culture chamber. The two chambers had separate inlets, and were partitioned from one another. The only communication between the supply chamber and the culture chamber was represented by the pores of the membrane. With an advantageous pore diameter of 0.1 to 5.0 µm, these pores were permeable for small molecules and proteins, but not for the cells. The overall device described in FIG. 1 ensured that gas and liquid can be passed continuously through the system.

The bioreactor system also included a mobile hardware unit, the pumps and compressors, as well as measuring and control units. Furthermore, this unit also included a drive motor and a rotary device, which permitted mounting and rotation of the plastic reactor.

Example 5

Functioning Principle

By means of the rotary device, the plastic reactor was turned around its axis of rotation in a rotation cycle that can be adapted to the respective cell line. This rotation cycle was advantageously repeated without interruption over the entire bioreactor run time. The eight phases of a rotation cycle are listed below by way of example.

Phase: rotation to the right by 180°
Phase: holding time
Phase: rotation to the right by 180°
Phase: holding time
Phase: rotation to the left by 180°
Phase: holding time
Phase: rotation to the left by 180°
Phase: holding time As the result of a rotation cycle, the reactor had performed one full revolution in one direction and one full revolution in the opposite direction and was once again disposed in the original starting position. The alternation of direction of rotation permits media and gas to flow through ports, which were integrated in fixed position in the reactor and to which plastic tubes were fixed. In contrast to the majority of mammalian-cell bioreactors, therefore, the system operated effectively without mobile structural components that project into the sterile supply or culture zone, such as impeller shafts or media and gas feed tubes. Thus, the associated contamination risk did not exist, and no expenses were incurred for safeguarding corresponding rubbing surfaces, for example by double rotating mechanical seals.

The system construction and mode of operation simultaneously ensured that every individual hollow-filament membrane was subjected to identical exposure conditions in both phases over the entire bioreactor run time, regardless of the number of such membranes in the system. The exposure in the gas phase primarily achieved the supply of oxygen, while the exposure in the liquid phase achieved primarily the uptake of dissolved nutrients and the discharge of metabolic products. Both nutrient medium and gas mixture can be fed continuously.

In summary, the present invention has the following advantageous features: 1) it provides a reactor with integrated cell retention system as disposable article, 2) the membrane is permeable for protein, permitting cell-free harvesting, 3) identical exposure conditions for every individual hollow-filament membrane in the system are provided, 4) short diffusion paths for oxygen during exposure in the gas phase, 5) no gradient formation in the gas phase of the exposure reactor over the length of the reactor, and 6) a plurality of gas ports, which are distributed appropriately over the end caps and which permit gas to flow through continuously even during rotation.

PCT patent application PCT/DE/2004/001248 filed Jun. 14, 2004, and provisional U.S. application No. 60/578,824 filed Jun. 14, 2004, are incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A method for initiation of growth and cultivation of cells, comprising:
   introducing said cells into culture compartments of a liquid-gas-phase exposure bioreactor comprising a supply chamber comprising hollow-filament membranes having an inside diameter of no larger than 5 mm, wherein an inner volume of said hollow-filament membranes forms said culture compartments;

filling approximately one half of said supply chamber with a nutrient medium and a remainder with a gas mixture, thereby obtaining a gas phase and a liquid phase;

turning on perfusion of medium and gas simultaneously or separately;

cyclically exposing said hollow-filament membranes and said cells contained therein to the gas or liquid phase.

2. The method according to claim 1, wherein said hollow-filament membranes are oriented horizontally, wherein after the reactor has been filled, about half of the membranes are covered with nutrient medium, and wherein cyclic exposure of the hollow-filament membranes is achieved by rotating the reactor 360° in one direction and then in the opposite direction.

3. The method according to claim 2, wherein the rotation takes place in two 180° steps, which are separated from one another by variably adjustable waiting times, so that each individual hollow-fiber membrane spends the same time in the liquid phase as in the gas phase.

4. The method according to claim 1, wherein the cyclic exposure is achieved by immersing the hollow-filament membranes in the nutrient medium and then lifting the hollow-filament membranes into the gas phase.

5. The method according to claim 1, wherein cells of low density are introduced into the culture chamber and grow to cells of high density.

6. The method according to claim 5, wherein cells of the lowest cell density are introduced into the culture chamber together with gels of cross-linked polypeptides, which have a high glutamine content, and/or with semisolid media of viscous fluids or fluids comprising microscopically small gel fragments.

7. The method according to claim 1, wherein the cells are protozoa, bacteria, yeasts, fungi, plant cells or mammalian cells.

8. The method according to claim 1, wherein the cells are introduced into the compartments via a central charging system outside the supply chamber; and wherein simultaneous and homogeneous input of the cells into all compartments is possible via one port in the supply chamber.

9. A method for preparing a compound, comprising:
introducing cells into the culture compartments of a device; wherein said device comprises:

a cylindrical two-phase supply chamber which can be charged with gas and a culture medium, parallel to the longitudinal axis of a shell of said supply chamber, polymeric, cell-retaining, microfiltering, hollow-filament membranes having an inside diameter of not more than 5 mm are fixed in an end plate, wherein the inner volumes of said hollow-filament membranes form culture compartments in which cells to be cultivated are disposed, wherein the supply chamber contains a gas phase through which a gas mixture can flow and a liquid phase through which said culture medium can flow;

wherein each hollow-filament membrane has a spacing of at least 0.5 mm to the neighboring hollow-filament membrane over the length of the cylinder;

wherein the hollow-filament membranes are symmetrically disposed relative to an imaginary cross section along the longitudinal axis of the cylinder;

wherein no membrane is disposed on the imaginary cross-sectional plane along the longitudinal axis of the cylinder;

wherein said device is capable of being used for initiation of growth and cultivation of cells;

filling approximately one half of said supply chamber with a nutrient medium and a remainder with a gas mixture, thereby obtaining a gas phase and a liquid phase;

turning on perfusion of medium and gas simultaneously or separately;

cyclically exposing said hollow-filament membranes and said cells contained therein to the gas or liquid phase, thereby growing and cultivating said cells, which produce cell products, cell constituents, viruses, proteins or low molecular weight substances;

introducing said cell products, cell constituents, viruses, proteins or low molecular weight substances through the membranes into the liquid phase in the supply chamber;

removing said liquid phase from the reactor; and separating said cell products, cell constituents, viruses, proteins or low molecular weight substances from said liquid phase.

10. The method according to claim 9, wherein said cell products are drugs or diagnostic reagents.

* * * * *